(12) United States Patent
Goodenough et al.

(10) Patent No.: US 9,526,471 B2
(45) Date of Patent: Dec. 27, 2016

(54) PHANTOM AND METHOD FOR IMAGE QUALITY ASSESSMENT OF A DIGITAL BREAST TOMOSYNTHESIS SYSTEM

(71) Applicant: THE PHANTOM LABORATORY, INCORPORATED, Greenwich, NY (US)

(72) Inventors: David J. Goodenough, Myersville, MD (US); Joshua R. Levy, Salem, NY (US)

(73) Assignee: THE PHANTOM LABORATORY, INCORPORATED, Greenwich, NY (US)

( * ) Notice: Subject to any disclaimer, the term of this patent is extended or adjusted under 35 U.S.C. 154(b) by 363 days.

(21) Appl. No.: 14/261,871

(22) Filed: Apr. 25, 2014

(65) Prior Publication Data

US 2015/0305705 A1    Oct. 29, 2015

(51) Int. Cl.
  *A61B 6/00*   (2006.01)
  *A61B 6/02*   (2006.01)
  *A61B 6/03*   (2006.01)

(52) U.S. Cl.
  CPC ............. *A61B 6/583* (2013.01); *A61B 6/025* (2013.01); *A61B 6/502* (2013.01); *A61B 6/58* (2013.01)

(58) Field of Classification Search
  CPC ........... A61B 6/025; A61B 6/502; A61B 6/58; A61B 6/583
  USPC ................................. 378/18, 37, 207, 22, 27
  See application file for complete search history.

(56) References Cited

U.S. PATENT DOCUMENTS

| | | | |
|---|---|---|---|
| 4,286,168 A | 8/1981 | Carr | |
| 4,843,866 A | 7/1989 | Madsen et al. | |
| 5,165,050 A | 11/1992 | Goodenough et al. | |
| 5,442,674 A * | 8/1995 | Picard | A61B 6/583 378/18 |
| 5,964,715 A * | 10/1999 | Thunberg | A61B 90/36 378/207 |
| 6,272,200 B1 * | 8/2001 | Pan | G06T 11/005 378/15 |

(Continued)

FOREIGN PATENT DOCUMENTS

| | | |
|---|---|---|
| DE | 19936409 A1 | 3/2001 |
| WO | 2014041469 A1 | 3/2014 |

OTHER PUBLICATIONS

International Search Report and Written Opinion for corresponding application No. PCT/US2015/025098 dated Jul. 3, 2015.

(Continued)

*Primary Examiner* — Allen C. Ho
(74) *Attorney, Agent, or Firm* — Heslin Rothenberg Farley & Mesiti P.C.

(57) ABSTRACT

A phantom for image quality assessment of digital breast tomosynthesis apparatus includes at least one set of beads arranged as a first ramp and as a second ramp in respective proximate parallel vertical planes in a reverse staircase pattern along a vertical direction with a final bead of the first ramp and an initial bead of the second ramp being located at substantially the same intermediate height within the phantom. The beads and additional test objects may be positioned in non-overlapping locations within the phantom to facilitate determination of multiple image quality parameters with a single scanning sequence of the phantom.

21 Claims, 8 Drawing Sheets

(56) References Cited

U.S. PATENT DOCUMENTS

| | | | |
|---|---|---|---|
| 6,466,638 B1* | 10/2002 | Silver | G06T 11/006 378/4 |
| 6,490,336 B1* | 12/2002 | Suess | A61B 6/032 250/252.1 |
| 6,626,569 B2* | 9/2003 | Reinstein | A61N 5/1048 250/252.1 |
| 6,715,918 B2 | 4/2004 | Mitschke et al. | |
| 7,016,456 B2* | 3/2006 | Basu | A61B 6/583 378/18 |
| 7,186,023 B2* | 3/2007 | Morita | A61B 6/466 378/18 |
| 7,286,631 B2 | 10/2007 | Li et al. | |
| 7,515,682 B2 | 4/2009 | Li et al. | |
| 7,582,860 B2* | 9/2009 | Kusunoki | A61B 6/583 250/252.1 |
| 7,780,351 B2* | 8/2010 | Heigl | A61B 6/032 378/207 |
| 7,950,849 B2 | 5/2011 | Claus et al. | |
| 8,043,003 B2* | 10/2011 | Vogt | G01N 23/046 378/207 |
| 8,075,183 B2 | 12/2011 | Thornton | |
| 8,104,958 B2* | 1/2012 | Weiser | A61B 6/583 378/162 |
| 8,215,836 B2 | 7/2012 | Beaumont et al. | |
| 8,220,994 B2* | 7/2012 | Heigl | A61B 6/547 378/207 |
| 2003/0058999 A1 | 3/2003 | Mitschke et al. | |
| 2013/0114799 A1 | 5/2013 | Yamakawa et al. | |

OTHER PUBLICATIONS

Brunner, Claudia C. et al., "Evaluation of Various Mammography Phantoms for Image Quality Assessment in Digital Breast Tomosynthesis", IWDM, 2012, pp. 284-291.

Vecchio, Sara et al., "Phantom design for image quality assessment in digital breast tomosynthesis", Center for Devices and Radiological Health, 2013, 1 page.

Van Engen, R. et al., "Protocol for the Quality Control of the Physical and Technical Aspects of Digital Breast Tomosynthesis Systems", European Reference Organisation for Quality Assured Breast Screening and Diagnostic Services, Feb. 2013, 58 pages.

Smith, Andrew, Ph.D., "Design Considerations in Optimizing a Breast Tomosynthesis System", Hologic, printout available online on Apr. 25, 2014 at: http://www.hologic.com/data/Design_Considerations_Optimizing_Breast_Tomo.pdf, 8 pages.

CTP700 Datasheet, printout available online on Apr. 25, 2014 at: http://www.phantomlab.com/library/pdf/CTP700_datasheet.pdf, p. 3.

Catphan 700 Manual, printout available online on Apr. 25, 2014 at: http://www.phantomlab.com/library/pdf/catphan700manual.pdf, p. 16.

CTP591 Bead Geometry Module, printout available online on Apr. 25, 2014 at: http://www.phantomlab.com/library/pdf/catphan600_download.pdf, p. 9.

Catphan 500 and 600 Manual, printout available online on Apr. 25, 2014 at: http://www.phantomlab.com/library/pdf/catphan500-600manual.pdf, p. 20.

* cited by examiner

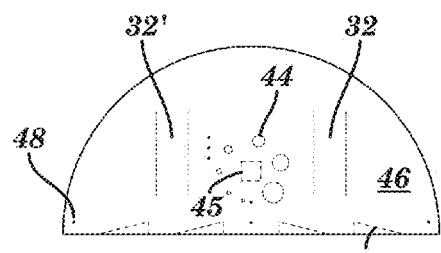 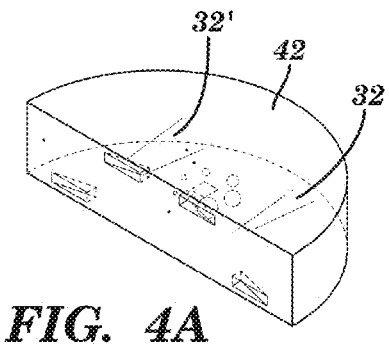
FIG. 4B    FIG. 4A
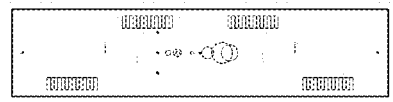 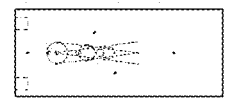
FIG. 4C    FIG. 4D
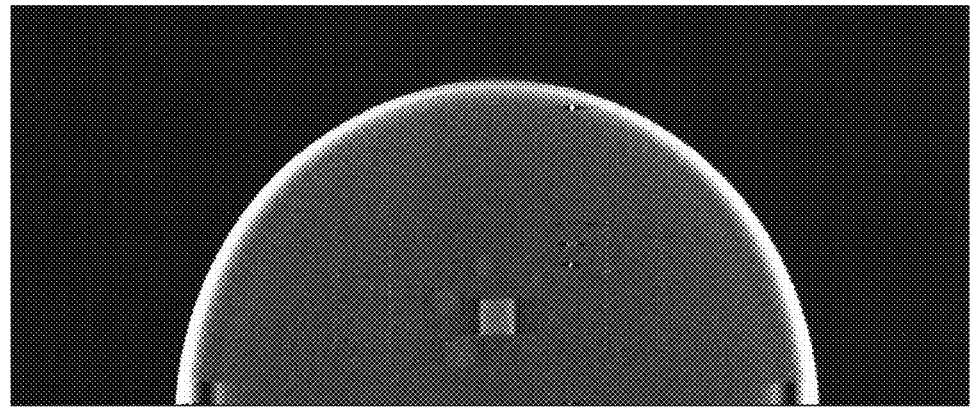
FIG. 5A

PHANTOM AND METHOD FOR IMAGE QUALITY ASSESSMENT OF A DIGITAL BREAST TOMOSYNTHESIS SYSTEM

BACKGROUND ART

The present invention relates generally to the field of image quality assessment of medical imaging systems and, more particularly, to a phantom and method of assessing imaging quality of a digital breast tomosynthesis system.

Breast cancer remains one of the most common cancers among women despite early detection methods such as breast self-examination, annual mammograms and clinical breast exams. The objective of screening mammography is to identify cancers while they are small and localized. However, some breast cancers still are missed while in their earliest stages, and it is widely agreed that imaging of dense breasts can be improved.

In conventional two dimensional film or full field digital mammography (FFDM), overlapping dense fibroglandular tissue within the breast can reduce the visibility of malignant abnormalities or simulate the appearance of an abnormality. This can lead to unnecessary patient recalls, biopsies and psychological stress. In addition, mammography is known to be less sensitive in women with dense breasts, who are at higher risk of developing breast cancer.

Digital breast tomosynthesis (DBT), also referred to as three-dimensional (3D) mammography, is a newly developed form of three-dimensional imaging with the potential to improve the accuracy of mammography by reducing tissue overlap. This overlap, which is sometimes known as anatomical noise, degrades image quality in standard 2D projection imaging and can mask suspicious areas.

In DBT, the breast is compressed, in the standard fashion, between a compression paddle or plate and a breast support plate overlying an image receptor/detector. With the breast kept stationary, an x-ray tube is moved in an arcuate or isocentric motion and a series of low-dose images, known as projections, are taken at different angular locations of the tube over a limited total angular range known as the scan angle. The projections undergo a reconstruction process using algebraic reconstruction algorithms to produce high resolution images, also known as tomographic sections or slices, in planes parallel to the breast support plate. The number of reconstructed slices will depend upon the thickness of the compressed breast and the desired separation between slices, which might typically be around 1 mm. These sections can be viewed on a work station, either as individual slices or sequentially in a dynamic video mode. By minimizing the superimposition of overlying breast tissue, DBT has the potential to differentiate malignant features more definitively from non-malignant ones.

Removal of confusing overlying tissue provides clearer imaging, better sensitivity and fewer patient recalls with DBT. Digital breast tomosynthesis also has the potential for lower radiation dosage and less breast compression. Significantly, by detecting breast cancer early, a woman's chances of survival are higher and she may have more treatment options available to her.

Tomosynthesis differs from computed tomography (CT) in several significant aspects. In DBT, projections are obtained over only a limited range of angles, while in CT, projections are obtained through either 180° or 360° rotations of x-ray tubes and detectors.

In conventional computed tomography (CT), a plane of interest is established by moving the detector and the x-ray tube in opposite directions. This establishes a plane of interest (or a plane of focus). Features within the plane of focus appear relatively sharp. A major disadvantage of this approach is that there is only a single plane of focus for each exposure and geometric configuration. Another disadvantage of CT imaging of the breast is the higher radiation dose involved in conventional system designs.

In contrast, in tomosynthesis, an arbitrary number of planes may be retrospectively reconstructed from a single sequence of projection images. Typically, a series of projection images is obtained while the x-ray tube moves in a limited arcuate or linear motion. (However, the motion of the x-ray tube could be more complex and the imaging detector could be stationary or moving.) After the acquisition sequence is complete, the projection images are combined by shifting and adding these together to bring a specific plane into focus. Different planes can be brought into focus by varying the amount of shifting. Advantages of tomosythesis over conventional projection imaging include: depth localization, improved conspicuity owing to the removal of the clutter caused by overlying tissue structures, and improved contrast of local structure by limiting the dynamic range to a single plane.

The differences between tomosynthesis and CT impose different requirements on phantoms and methods of assessing image quality in the two different imaging modalities. As opposed to relatively well defined slices with finite extension in CT, tomosynthesis slices are less well defined with some degree of extension from the center of the slice of interest to the boundaries of the object being considered. Due to their disparate methods of reconstruction, artifacts and image problems are very different in tomosynthesis as compared to CT, and new and different approaches to the measurement of image quality in tomosynthesis are needed.

In a recent study, entitled "Evaluation of Various Mammography Phantoms for Image Quality Assessment in Digital Breast Tomosynthesis" by Claudia Brunner et al, four different existing mammography phantoms were investigated for their appropriateness for image quality evaluation in Digital Breast Tomosynthesis. This study concluded that, "Although each phantom under study has its advantages, none of them allows a thorough quality evaluation of reconstructed tomosynthesis images". It can also be noted from this study, that modulation transfer function (MTF) data is only available from transforming edge response function in one direction at a time, and no point source for 2D information and 2D MTF transform is available. Cited deficiencies in all phantoms studied include slice sensitivity profile.

In a "Protocol for the Quality Control of the Physical and Technical aspects of Digital Breast Tomosynthesis Systems", draft version 0.10, published in February 2013, by the European Reference Organisation for Quality Assured Breast Screening and Diagnostic Services (EUREF), a phantom for z-resolution in DBT is disclosed that comprises a planar array of 25 spaced apart aluminum spheres. In use, this phantom, must be repositioned and exposed at multiple different heights in a time consuming and repetitive procedure.

The present invention provides a phantom and method of image quality assessment specifically tailored and optimized for digital breast tomosynthesis systems.

BRIEF SUMMARY OF THE INVENTION

According to the present invention, a phantom for calibrating a tomosynthesis imaging system includes at least one set of beads arranged as a first ramp and a second ramp in respective proximate parallel vertical planes in a reverse staircase pattern along a vertical direction, with a final bead of the first ramp and an initial bead of the second ramp being located at substantially the same intermediate height within the phantom. The reverse staircase pattern may include a first ramp of spaced apart beads disposed in a first vertical plane and extending from a lower end of the first ramp along a first inclination up to a final end of the first ramp at an intermediate height of the phantom, and a second ramp of spaced apart beads disposed in a second vertical plane and extending from near the final end of the first ramp at the intermediate height up and back along a second inclination. The second vertical plane is located parallel to, and spaced from, the first vertical plane.

The second vertical plane may be located adjacent the first vertical plane, and the beads of the second plurality do not vertically overlap the beads of the first plurality.

The beads of the first plurality and/or of the second plurality may be spherical and may be identical in size. Each bead preferably has a size smaller than or comparable to resolution size of the imaging system or a small size, the impact of which may be calculated and used to correct (deconvolve) the effect of the bead size on the measured slice width of the tomosynthesis system. Each bead may comprise a solid sphere of metal or other material having a signal strength within a dynamic range of the imaging system, and may have a size and composition to minimize artifact spread function in other z-axis image planes. Center-to-center spacing of adjacent beads in the first plurality and/or the second plurality should be sufficient to avoid streaking of the beads into one another in an imaging plane.

The first ramp of beads and the second ramp of beads of the phantom may be embedded in a uniform material that mimics x-ray attenuation of breast tissue. Preferably, full horizontal extend of the first ramp in the first vertical plane is substantially equal to full horizontal extent of the second ramp in the second vertical plane.

The phantom may advantageously include at least one additional test object located in a position so as not to vertically overlap with the beads. The additional test object may include at least one of: spheres of different diameters, a square, for example, of thin Aluminum, fiducial markers, and at least one graded step incrementation ruler to measure missing tissue at a simulated chest wall.

The first ramp and the second ramp of beads and the at least one additional test object preferably comprise a single test module of the phantom. The phantom may also include a blank non-structured module and/or a structured module that simulates a breast pattern. The additional module(s) may serve as a spacer for the test module.

In another aspect of the present invention, the phantom may include at least two sets of beads, each being arranged as a first ramp and a second ramp in respective proximate parallel vertical planes in a reverse staircase pattern along the vertical direction, the at least two sets being horizontally spaced apart on opposite sides of the phantom, with the first ramp of the first set ascending in a first direction and the first ramp of the second set ascending in an opposite direction.

The present invention also contemplates a method for image quality assessment of a tomosynthesis imaging system. The method may include providing a phantom having at least one set of beads arranged as a first ramp and a second ramp in respective proximate parallel planes in a reverse staircase pattern along a vertical direction with a final bead of the first ramp and an initial bead of the second ramp being located at substantially the same intermediate height within the phantom, scanning the phantom with the tomosynthesis imaging system; and, with results of scanning of the at least one set of beads, determining slice sensitivity profile along the vertical direction and at least one of: point spread function of at least one bead in a horizontal plane, or line spread function of at least one bead in the horizontal plane, or a two-dimensional modulation transfer function as a function of spatial frequency. This determining may, advantageously, be based on a single scanning sequence of the phantom, and is preferably automated.

According to another aspect of the invention, the slice sensitivity profile may be determined by plotting peak intensity of each bead as a function of bead vertical position, or integrating total bead intensity at each bead vertical position, or deriving a metric of bead intensity values as a function of each bead vertical position.

According to a further aspect of the invention, the phantom may further includes a square, and the method may further include determining at least one of line spread function or modulation transfer function from scanning the square.

The present invention further contemplates a method for image quality assessment of a digital breast tomosynthesis imaging system employing a phantom having a first ramp of spaced apart beads disposed in a first vertical plane and extending from a lower end of the first ramp along a first inclination up to a final end of the first ramp at an intermediate height of the phantom, a second ramp of spaced apart beads disposed in a second vertical plane, parallel and proximate the first vertical plane, and extending from near the final end of the first ramp at the intermediate height up and back along a second inclination, spheres of different diameters, a square, fiducial markers, and at least one graded step incrementation rule, all embedded, in a uniform material, in a single test module. The method may include scanning this phantom with the tomosynthesis imaging system; and, with results of said scanning, determining by automated analysis: slice sensitivity profile along a vertical direction from the beads, point spread function and corresponding modulation transfer function of at least one bead in a horizontal plane, contrast detail from the spheres of different diameters, low contrast contrast-to-noise ratio from the square, geometric distortion from the fudicial markers, and missed tissue at a simulated chest wall using the at least one graded step incrementation ruler.

BRIEF DESCRIPTION OF THE DRAWING FIGURES

These and other aspects, features and advantages of the present invention will be readily apparent from the following detailed description, when read in conjunction with the accompanying drawing figures, in which:

FIG. 4A is a perspective view of a phantom for image quality assessment of digital breast tomosynthesis apparatus according to the present invention;

FIG. 4B is a top plan view of the phantom of FIG. 4A;

FIG. 4C is a front elevation view of the phantom of FIG. 4A;

FIG. 4D is a side elevation view of the phantom of FIG. 4A;

Figure 5B:
Figure 5C:
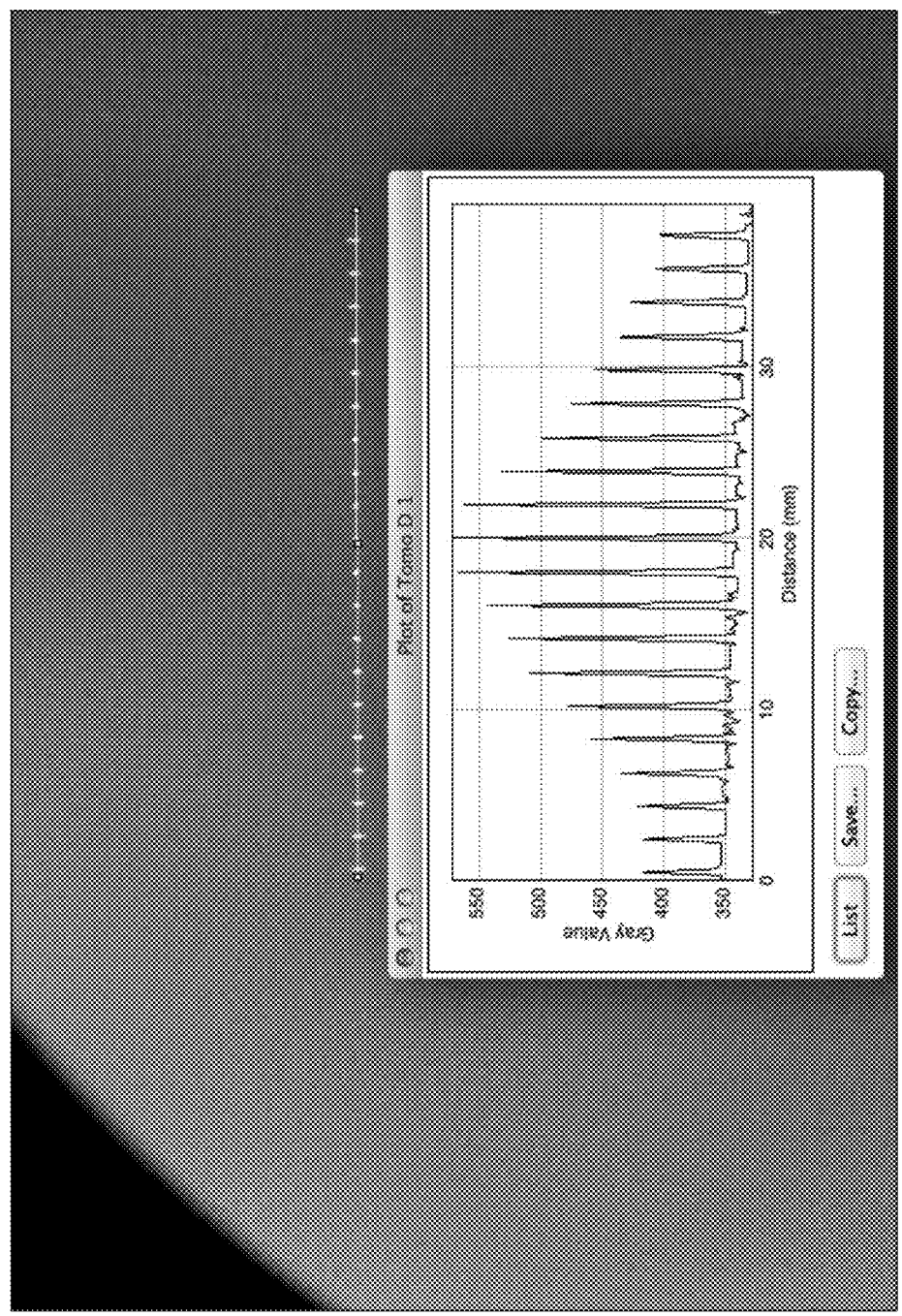
Figure 5D:
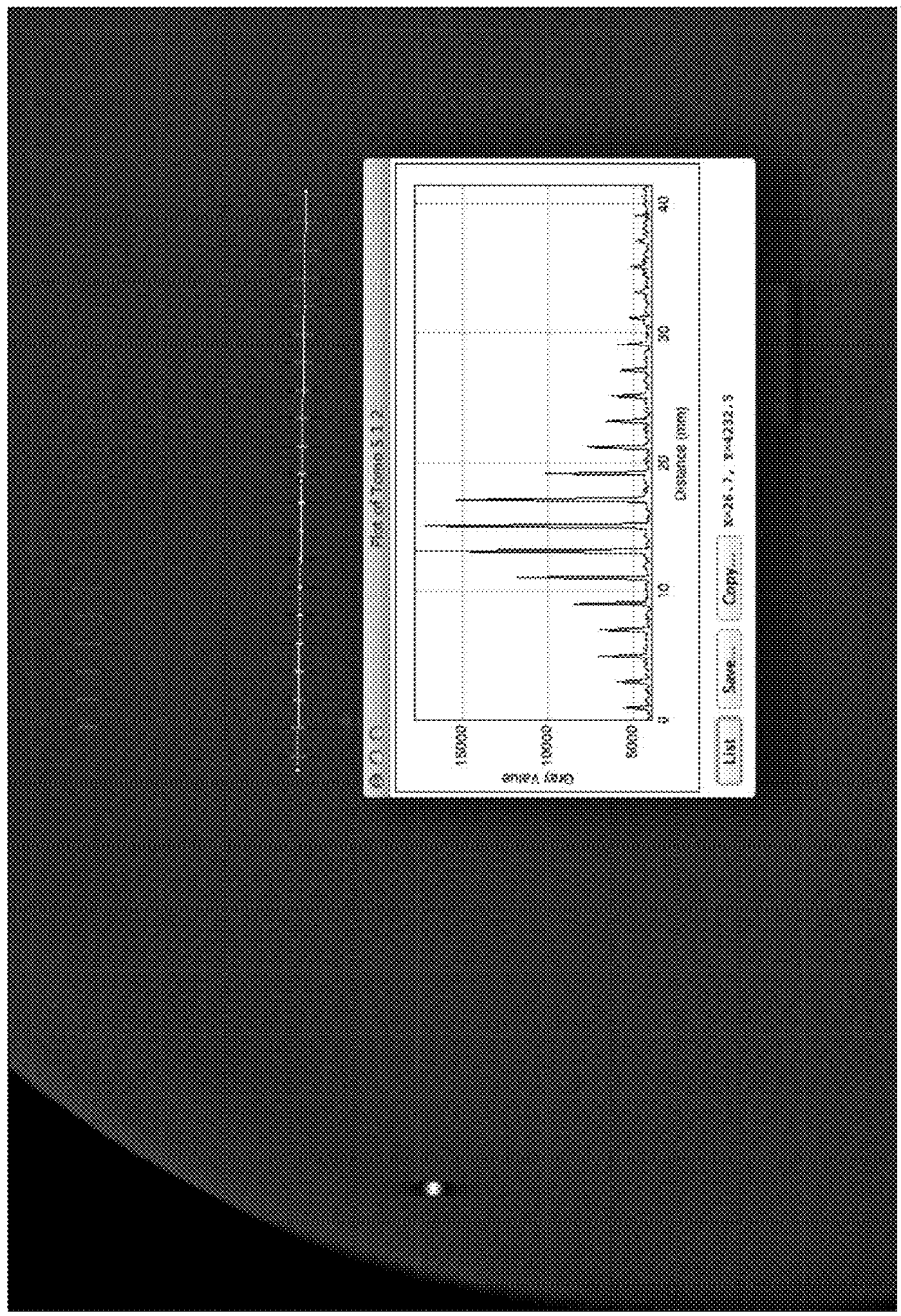
Figure 6:
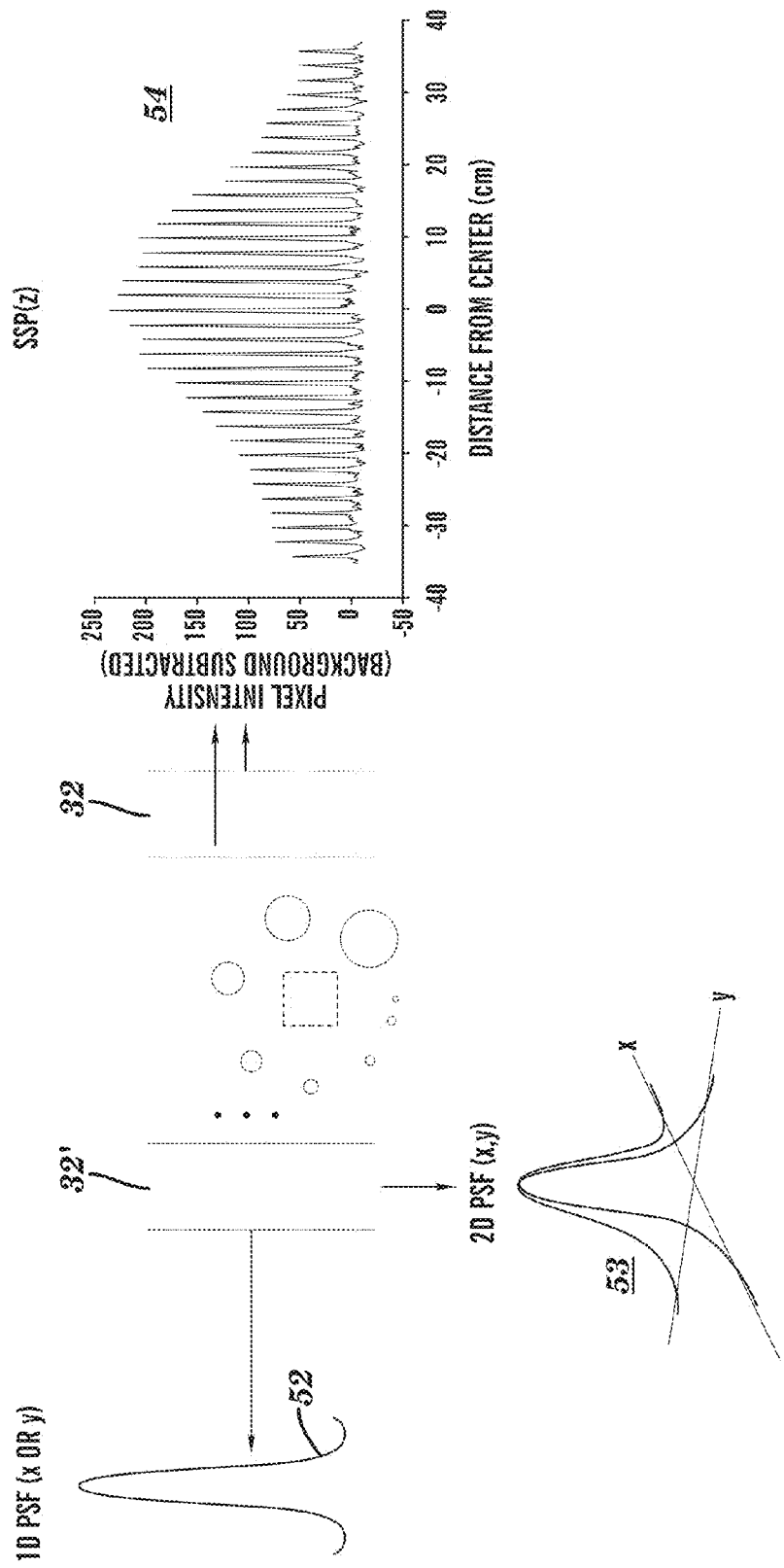

FIG. 5A is an image of a slice reconstructed from the phantom of FIG. 4A; FIG. 5B is a tomosynthesis image of the bead ramps; FIGS. 5C and 5D are profiles through the bead ramps for different 1 mm thick slices; and FIG. 6 is a diagram illustrating the determination of point spread function (x or y direction), 2D point spread function (x,y), and slice sensitivity profile (z direction) from the beads of the phantom of the present invention. The profile is "folded" at the common plane of the reverse staircase arrangement of beads.

DETAILED DESCRIPTION

According to the present invention, a phantom for image quality assessment of a digital breast tomosynthesis imaging system includes at least one set of spaced apart beads arranged as a first ramp and a second ramp in respective proximate parallel vertical planes in a reverse or folded staircase pattern along a vertical (z) direction with a final bead of the first ramp and an initial bead of the second ramp being located at substantially the same intermediate height within the phantom. This arrangement of beads facilitates automated determination of in-plane (x, y; also sometimes referred to herein as horizontal) spatial resolution and slice thickness in the z direction (also sometimes referred to herein as the vertical or z axis direction). Each bead is not only a source of data for a point source response function, that can be measured in real space (x, y), but also the resulting intensity data can be Fourier Transformed to provide a two dimensional 2D modulation transfer function (x, y) and/or line spread functions. In addition, the plurality of beads in the reverse staircase pattern provides points for a slice sensitivity profile along the z axis-SSP(z). The SSP can be achieved by plotting peak intensity of each bead as a function of bead vertical (z) position, integrating total bead intensity at each bead vertical position, or deriving a metric of bead intensity values as a function of each bead vertical position.

One or more test objects may be embedded in a single test module of the phantom, along with the beads, without overlapping the beads, facilitating comprehensive and automated image quality assessment with a single scanning sequence.

Figure 1:
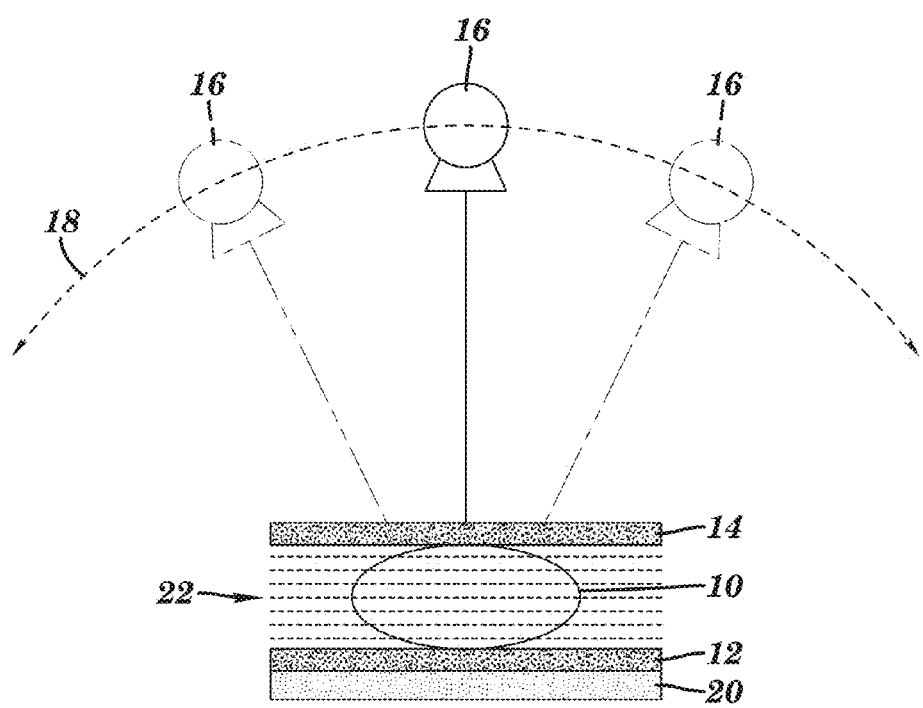
FIG. 1 is a schematic illustration of image acquisition with a digital breast tomosynthesis imaging system.

FIG. 1 schematically illustrates the acquisition of images in a digital breast tomosynthesis system. The breast 10 is compressed between a breast support plate 12 and a compression paddle or plate 14. In known fashion, an x-ray source or tube 16 moves along a limited arc length 18. The breast attenuated x-rays are detected by a digital detector or image receptor 20 located beneath the breast support plate 12. In this way, a series of low dose images are acquired at different angles. Image planes or slices 22, parallel to the breast support plate 12, are then reconstructed, in known fashion, e.g., from algebraic reconstruction algorithms implemented in a computer processor (not shown), and may be viewed individually or in a dynamic video mode, e.g. at a workstation (not shown).

The path of movement of the x-ray source 16 may be arcuate, isocentric, linear or have a more complex form. The digital detector 20 may be stationary or may rotate opposite to the x-ray source 16. Digital breast tomosynthesis equipment has been approved for cancer screening by the Federal Drug Administration and some versions are commercially available while others are currently under development.

Advantageously, DBT overcomes the overlapping problem associated with traditional two-dimensional mammography and provides for clearer imaging, better sensitivity, fewer patient recalls and the potential for lower dose and less breast compression. As a result, visualization and earlier detection of calcifications, masses, architectural distortions and asymmetries are possible, leading to earlier and more effective treatment, when appropriate The total radiation dose from a DBT imaging sequence may be similar to that of traditional two-dimensional mammography.

According to the present invention, a phantom specifically tailored to the unique characteristics of digital breast tomosynthesis is provided. The phantom may advantageously be employed to test, calibrate and/or assess image quality of the digital breast tomosynthesis apparatus.

Figure 2:
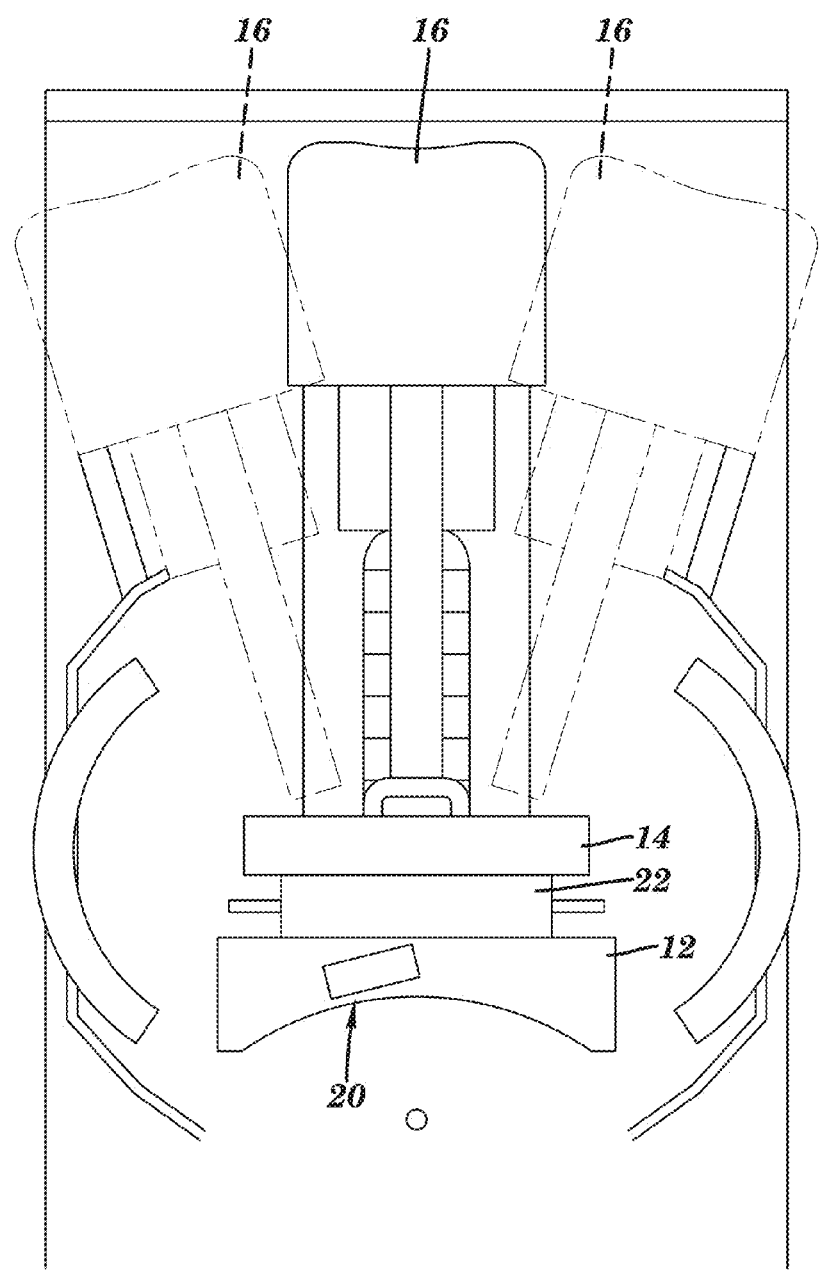
FIG. 2 illustrates the use of a phantom to test, calibrate and/or assess image quality of a digital breast tomosynthesis system.

As illustrated in FIG. 2, a phantom 22 is located between the compression paddle or plate 14 and the breast support plate 12 of the DBT equipment. In the illustrated example, a digital detector or image receptor 20 rotates in alignment with the position of the moving x-ray source 16. For illustrative purposes, only three positions of the x-ray source 16 are shown. The x-ray source 16 may provide a narrow x-ray beam and the x-ray field can be collimated to the digital detector or image receptor 20.

The phantom 22 of the present invention may be used in DBT apparatus in which the digital detector or image receptor 20 is stationary or in which both the x-ray source 16 and the digital detector or image receptor 20 rotate about a common axis, or in other DBT equipment arrangements.

Figure 3A:
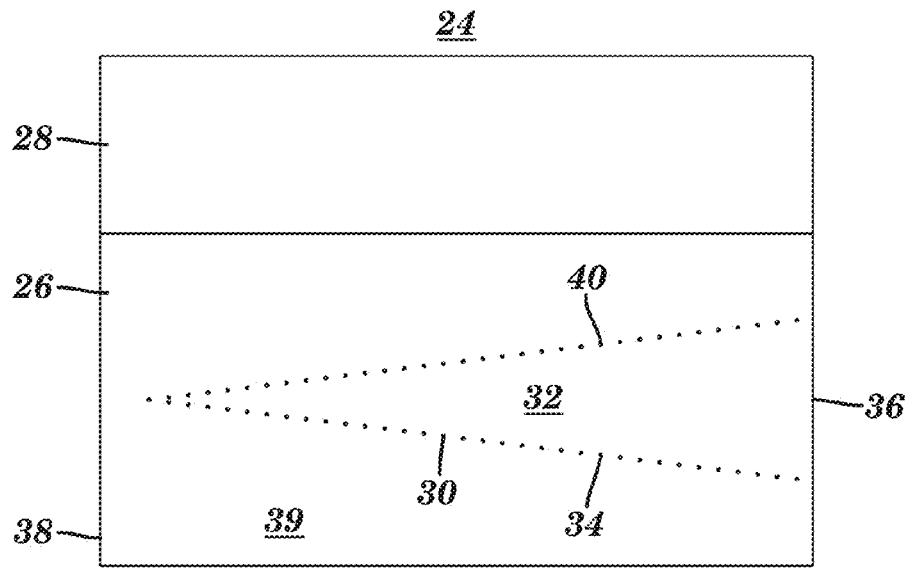
FIG. 3A is a simplified side view of a phantom employing a reverse staircase pattern of beads according to the present invention.
Figure 3B:
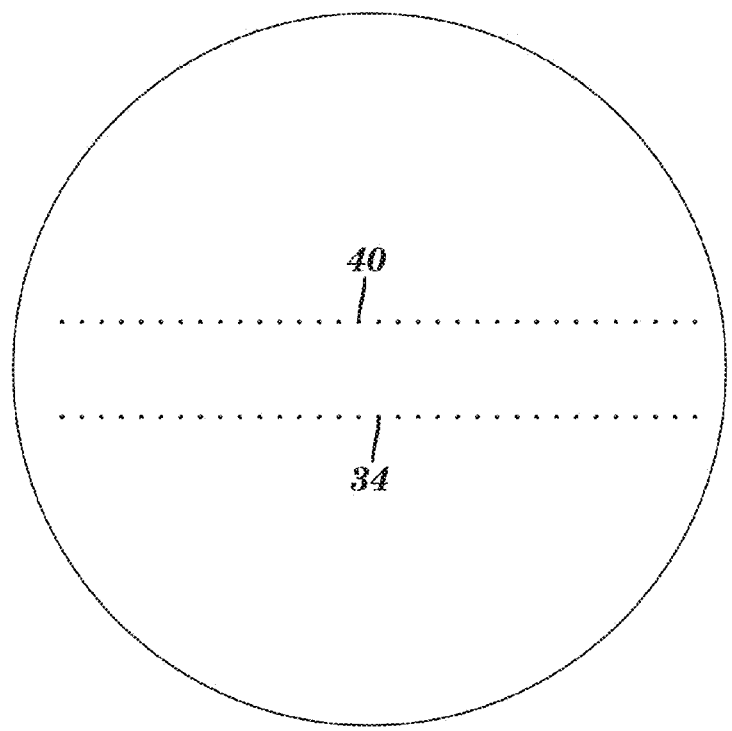
FIG. 3B is a top plan view of the phantom of FIG. 3A.

FIGS. 3A and 3B provide a simplified view of a phantom 24 for image quality assessment of digital breast tomosynthesis (DBT) apparatus, in accordance with the principles of the present invention. The phantom 24 includes a test module 26 and a spacer 28 which can be located above or below test module 26. The spacer 28 may comprise a blank non-structured module or a structured module that simulates a breast pattern.

Phantom 24 may include one or more spacers 28 to vary the height or thickness of test module 26. Spacer(s) 28 may be separate from, affixed to, or integral with test module 26. Both spacer 28 and test module 26 preferably comprise a uniform material that mimics the x-ray attenuation of breast tissue. The test module 26 may, for example, comprise a 2.8 cm thick D shaped slab, with added spacer(s) of 1.4 cm thickness.

Test module 26 includes at least one set of beads 30 arranged in a reverse or folded staircase pattern 32. The reverse or folded staircase pattern 32 includes a first ramp 34 of spaced apart beads 30 disposed in a first vertical plane along a first inclination extending from near a first side 36 of the phantom 24 up to an intermediate height near a second opposite side 38 of the phantom 24, and a second ramp 40 of spaced apart beads 30 disposed in a second vertical plane along a second inclination extending from near the second opposite side 38 at substantially the intermediate height up and back towards the first side 36 of the phantom 24. The second vertical plane is located parallel to and spaced from the first vertical plane, as illustrated in the top plan view of FIG. 3B.

Preferably, the second vertical plane is located adjacent the first vertical plane and the beads 30 of the second ramp 40 do not vertically overlap the beads 30 of the first ramp 34.

The beads 30 of the first ramp 34 and the second ramp 40 may be identical in size and are preferably spherical. Each bead, advantageously, may have a size smaller than or comparable to resolution of the imaging system, or a known size that may be compensated in any measurement(s) involving the bead(s), for example, used to correct (deconvolve) the effect of the bead size on the measured slice width of the Tomosynthesis system.

The beads 30 may comprise a solid sphere of metal or other material having a signal strength within a dynamic range of the imaging system. Adjacent beads are spaced to avoid bead streaking into one another in an image plane.

The size, center-to-center spacing, and location of the beads 30 within the test module 26 are chosen such that the signals will not be over-ranged and such that each bead is highly reproducible in size, shape, and position. The beads 30 are also sized to individually serve as a point source for in-plane point source function determination and to facilitate slice thickness and slice location determination.

In an exemplary embodiment, the reverse or folded staircase pattern 32 may be formed from 50 spherical beads 30 of tungsten carbide each having a diameter of 0.007 inches (0.18 mm) with a center-to-center vertical spacing of 0.25 mm between adjacent beads (including between the last bead of the first ramp 34 and the first bead of the second ramp 40) and center to center spacing in the transverse (x,y) plane of 2 mm, and an inclination angle of 7.1 degrees. The number, size, composition, spacing of the beads 30 and the inclination angle of the bead ramps may vary.

The beads 30 are preferably precisely located within the surrounding medium 39 by encapsulation, machining or other techniques. The surrounding medium 39 preferably mimics the x-ray attenuation of breast tissue and may comprise, for example, materials enumerated in "Tissue Substitutes in Radiation Dosimetry and Measurement", International Commission of Radiation Units and Measurements, ICRU report 44, 1989.

Advantageously, the reverse or folded staircase pattern 32 of beads 30 may be employed with other test objects in a single test module 26 of a phantom 42, as illustrated in FIGS. 4A-4D. In the illustrated embodiment, phantom 42 includes two reverse or staircase patterns 32, 32' of beads 30, with the patterns being spaced apart horizontally from one another on opposite sides of the phantom 42. The beads within each pattern 32, 32' may be identically or differently sized and/or identically or differently spaced from each other. The two ramps of one pattern of beads preferably extend in opposite directions to the corresponding ramps of the other pattern such that the second pattern 32' comprises a mirror image of the first pattern 32 of beads, as seen from the side in FIG. 4D. The beads in the first pattern 32 may advantageously be offset from the beads of the second pattern 32' by ½ the center to center z-axis inter-bead spacing to double the z-axis sampling for the beads.

The DBT phantom 42 may include one or more additional test objects located in positions so as to not vertically overlap with the beads 30 of the first and second patterns 32, 32'. The additional test objects may comprise: spheres 44 of different diameters (e.g. 1 mm, 1.5 mm, 2, 3, 4, 6, 8, 10 mm acrylic beads) for low contrast study, arranged in a circular or spiral pattern; a square 45, for example, a 1 cm² square, thin (0.2 mm thick) aluminum sheet for signal to noise and contrast to noise studies; 1 mm diameter Aluminum spheres 48 for four fiducial markers of spatial position, and for three markers for depth position; and at least one graded step incrementation ruler 50 for measuring missing tissue at a simulated chest wall. Illustrated in FIGS. 4A-4D, are 4 rulers, each with twelve 0.5 mm stops for a total of 6 mm intrusion from a simulated chest wall. The size of the rulers are 6 mm by 2 mm wide. Of course, other test objects, and different sizes, positions, compositions and combinations of test objects might also be employed in the test module.

Preferably, the beads and all of the other test objects are embedded in a uniform material 46 that mimics x-ray attenuation of breast tissue, in a single test module. The phantom 42 may be D-shaped to roughly approximate the shape of a compressed breast. In one example, the test objects were embedded in a urethane material having the semi-circular or D-shape, with a total phantom thickness of 4.2 cm, including a 1.4 cm thick spacer.

As illustrated, the test objects are located within the phantom so that they do not vertically overlap or compete with each other. This phantom may be used to determine:

slice sensitivity profile SSP(z) (i.e., slice width and slice location) using the angled ramps of small beads in the reverse staircase pattern;

homogeneity and Noise Power Spectrum (NPS) using the uniform area;

low contrast CNR (contrast-to-noise ratio), line spread function and modulation transfer function (via the well known Edge Response Function) using the Aluminum square;

contrast detail detectability using the spheres of varying diameters;

missed tissue at the chest wall using the graded step incrementation ruler(s);

geometric distortion using the fiducial markers at known distances and locations;

high contrast resolution using the small bead point source for point spread function, line spread function and/or modulation transfer function; and additional effects of increased breast thickness or structure using blank or structured spacers.

FIG. 5A depicts a representative slice through the phantom 42 of FIG. 4A, employing the non-overlapping multiple test objects, as reconstructed by DBT apparatus. FIG. 5B is a tomosynthesis image of the bead ramps in a reverse or folded staircase pattern 32, while FIGS. 5C and 5D depict profiles through the bead ramps for different 1 mm thick slices.

Using beads 30 of known size and position arranged in a reverse or folded staircase pattern 32 facilitates examination either visually and/or via computer analysis to determine aspects of in-plane (x, y) spatial resolution and aspects of slice thickness in the z axis to yield the slice sensitivity profile, SSP (z). The beads 30 may be arranged and positioned within the phantom to minimize competition with other test structures. In addition, the variation in the x, y plane of each pair of ramps in the reverse or folded staircase pattern 32 can be kept small so that the in-plane variations are minimized in their impact on the z axis results.

Each bead is not only a source of data for a point source function (PSF), that can be measured in real space 2D (x, y), but also the resulting intensity data can be reduced to a 1D Line Spread Function, LSF and/or Fourier Transformed to provide a 2D modulation transfer function ($v_x$, $v_y$), MTF. The MTF's can be corrected for both pixel size and bead size and MTF(x) and MTF(y) generated. Additionally, the MTF's can be inverse Fourier transformed to obtain the corresponding line spread functions—LSF(x), LSF(y) and resulting full width at half maximum, FWMH.

In addition, the pluralities of beads 30 in the reverse or folded staircase pattern 32 also provide points for the slice sensitivity profile along the z axis-SSP (z). The SSP can be obtained by (a) plotting peak intensity of each bead as a function of bead vertical position, (b) integrating total bead intensity at each bead vertical position, or (c) deriving a metric of bead intensity values as a function of each bead vertical position. Data from the two parts of the ramp can be "folded" around the common plane of reversal.

The derivation of 1D PSF (x or y), 2D PSF (x,y), and SSP (z) from the beads 30 in the reverse or folded staircase patterns 32, 32' is graphically illustrated in FIG. 6. Plot 52 represents the point spread function of an individual bead from which can be derived line spread function and modulation transfer function (x,y). Plot 53 illustrates 2D PSF (x,y). Plot 54 presents the peak intensity of a reverse or folded staircase pattern 32 of beads 30 from which SSP (z) can be derived. Note that the profile is folded when the reverse or folded staircase pattern 32 changes direction.

According to the present invention, a method for image quality assessment of a tomosynthesis imaging system includes scanning a phantom, having at least one set of beads 30 arranged as a first ramp 34 and a second ramp 40 in respective proximate parallel planes in a reverse or folded staircase pattern 32 along a vertical direction with a final bead of the first ramp 34 and an initial bead of the second ramp 40 being located at substantially the same intermediate height within the phantom 24, with the tomosynthesis imaging system; and, with results of scanning of the at least one set of beads 30, determining slice sensitivity profile along the vertical direction, and at least one of: point spread function of at least one bead in a horizontal plane, or line spread function of least one bead in a horizontal plane or a two-dimensional modulation transfer function as a function of spatial frequency. Advantageously, such determining can be based on a single scanning sequence of a single test module of the phantom, and may be automated, i.e. implemented with a computer processor.

When the phantom 42 of FIG. 4A is scanned with the tomosynthesis imaging system, the results of this scanning facilitates determination by automated analysis of: slice sensitivity profile along a vertical (z) direction from the beads 30, point spread function and corresponding modulation transfer function of at least one bead in a horizontal (x, y) plane, contrast detail from the spheres 44 of different diameters, low contrast contrast-to-noise ratio from the square 45, geometric distortion from the fiducial markers, and missed tissue at a chest wall using the at least one graded step incrementation ruler 50. Such comprehensive assessment of image quality is available from a single scanning sequence of the phantom 42. Of course, other test objects may be included in the phantom 42 to provide additional information, if desired.

The phantom of the present invention provides numerous advantages. Both separate and combined measurement of axial (x, y) resolution and z axis resolution, via slice width and SSP (z), can be achieved with the reverse staircase arrangement of beads. Moreover, challenges of limiting the x, y variation of the ramps by using the reverse or folded staircase pattern 32 allow the SSP (z) to be minimally impacted by x, y variation. Further, the reverse staircase design allows these ramps to be placed in a typical D-shaped phantom leaving enough space for other test objects and minimizing competition from these other structures in the phantom. Moreover, unlike other methods (using, for example, the phantom of the earlier referenced Protocol for the Quality Control of the Physical and Technical Aspects of Digital Breast Tomosynthesis Systems), wherein the phantom must be multiply scanned at different heights, the z-axis position of the current phantom as a whole does not have to be varied and multiply scanned in order to measure the SSP(z).

Then too, the use of a small bead as a point source allows determination of 2D information of Point Spread Function PSF (x,y) and this allows visualization of differences in x vs y effect of spatial resolution as results, for example, from preferential direction of tube movement. This 2D property is advantageous over only 1D line spread function information as obtained from other approaches, for example, U.S. Pat. No. 7,286,631 B2.

Embedding multiple non-overlapping test objects in the single test module of the phantom permits quick, accurate, comprehensive and automated image quality assessment with a single scanning sequence. Other advantages and benefits of the present invention will be readily apparent to those skilled in this art from the foregoing detailed description.

The invention claimed is:

1. Phantom for image quality assessment of a tomosynthesis imaging system, comprising:
a first ramp of spaced apart beads disposed in a first vertical plane and extending from a lower end of the first ramp along a first inclination up to a final end of the first ramp at an intermediate height of the phantom;
a second ramp of spaced apart beads disposed in a second vertical plane and extending from near the final end of the first ramp at the intermediate height up and back along a second inclination; and
wherein the second vertical plane is located parallel and proximate to the first vertical plane.

2. The phantom of claim 1, wherein the beads of the second ramp do not vertically overlap the beads of the first ramp.

3. The phantom of claim 2, wherein the beads of the first ramp and/or of the second ramp are identical in size.

4. The phantom of claim 1, wherein the beads of both the first ramp and the second ramp are spherical.

5. The phantom of claim 4, wherein each bead has a size smaller than or comparable to the resolution of the tomosynthesis imaging system.

6. The phantom of claim 5, wherein each bead comprises a solid sphere of metal having a signal strength within a dynamic range of the tomosynthesis imaging system.

7. The phantom of claim 5, wherein center-to-center spacing of adjacent beads in the first ramp and/or the second ramp is sufficient to avoid bead streaking into one another in an image plane.

8. The phantom of claim 1, further comprising at least one additional test object located in a position so as not to vertically overlap with the beads of the first ramp or the beads of the second ramp.

9. The phantom of claim 8, wherein said at least one additional test object comprises at least one of: spheres of different diameters, or a square, or fiducial markers, or at least one graded step incrementation rule.

10. The phantom of claim 8, wherein said at least one additional test object comprises: spheres of different diameters, a square, fiducial markers, and at least one graded step incrementation ruler, all embedded, along with the spaced apart beads of the first ramp and the second ramp, in a uniform material, in a single test module.

11. The phantom of claim 8, wherein the first ramp and the second ramp of spaced apart beads, and the at least one additional test object comprise a single test module of the phantom.

12. The phantom of claim 11, further comprising at least one of: (a) a blank non-structured module, or (b) a structured module that simulates a breast pattern, serving as a spacer for the single test module.

13. The phantom of claim 1, further comprising a uniform material that mimics x-ray attenuation of breast tissue, wherein the first ramp of spaced apart beads and the second ramp of spaced apart beads are embedded in the uniform material, and full horizontal extent of the first ramp in the first vertical plane is substantially equal to full horizontal extent of the second ramp in the second vertical plane.

14. A phantom for calibrating a tomosynthesis imaging system, comprising: at least one set of beads arranged as a first ramp and as a second ramp in respective proximate parallel vertical planes in a reverse or folded staircase pattern along a vertical direction with a final bead of the first ramp and an initial bead of the second ramp being located at substantially the same intermediate height within the phantom.

15. The phantom of claim 14, wherein the at least one set of beads comprises at least two sets of beads, each set of the at least two sets of beads being arranged in a first ramp and in a second ramp in respective proximate parallel vertical planes in a reverse or folded staircase pattern along the vertical direction, the at least two sets of beads being horizontally spaced apart on opposite sides of the phantom, with the first ramp of a first set of the at least two sets of beads ascending in a first direction and the first ramp of a second set of the at least two sets of beads ascending in an opposite direction.

16. A method for image quality assessment of a tomosynthesis imaging system, comprising:
  scanning the phantom of claim 14 with the tomosynthesis imaging system; and
  with results of scanning of the at least one set of beads, determining slice sensitivity profile along the vertical direction, and at least one of: point spread function of at least one bead in a horizontal plane, or line spread function of at least one bead in the horizontal plane, or a two dimensional modulation transfer function as a function of spatial frequency.

17. The method of claim 16, wherein said determining is based on a single scanning sequence of the phantom.

18. The method of claim 16, wherein determining the slice sensitivity profile comprises at least one of: (a) plotting peak intensity of each bead as a function of bead vertical position, or (b) integrating total bead intensity at each bead vertical position or (c) deriving a metric of bead intensity values as a function of each bead vertical position.

19. The method of claim 16, wherein the determining step is automated.

20. The method of claim 16, wherein the phantom further includes a square, and the method further includes determining at least one of line spread function or modulation transfer function from scanning the square.

21. A method for image quality assessment of a digital breast tomosynthesis imaging system, comprising:
  scanning the phantom of claim 10 with the tomosynthesis imaging system; and
  with results of said scanning, determining by automated analysis: slice sensitivity profile along a vertical direction from the spaced apart beads of the first ramp and the second ramp, point spread function and corresponding modulation transfer function, of at least one bead in a horizontal plane, contrast detail from the spheres of different diameters, low contrast contrast-to-noise ratio from the square, geometric distortion from the fiducial markers, and missed tissue at a chest wall using the at least one graded step incrementation ruler.

* * * * *